(12) United States Patent
Baldet

(10) Patent No.: US 12,193,379 B2
(45) Date of Patent: Jan. 14, 2025

(54) COANDA EFFECT FLOW BOOSTER AND AERAULIC DEVICE COMPRISING SUCH A FLOW BOOSTER

(71) Applicants: SYNGENTA CROP PROTECTION AG, Basel (CH); Institut national de recherche pour l'agriculture, l'alimentation et l'environnement, Paris (FR); ASUR Plant Breeding, Estrées-Saint-Denis (FR)

(72) Inventor: Patrick Baldet, Pressigny les Pins (FR)

(73) Assignees: SYNGENTA CROP PROTECTION AG, Basel (CH); Institut national de recherche pour l'agriculture, l'aliment, Paris (FR)

(*) Notice: Subject to any disclaimer, the term of this patent is extended or adjusted under 35 U.S.C. 154(b) by 80 days.

(21) Appl. No.: 18/016,341

(22) PCT Filed: Jul. 27, 2021

(86) PCT No.: PCT/FR2021/051400
§ 371 (c)(1),
(2) Date: Jan. 14, 2023

(87) PCT Pub. No.: WO2022/023663
PCT Pub. Date: Feb. 3, 2022

(65) Prior Publication Data
US 2023/0270066 A1    Aug. 31, 2023

(30) Foreign Application Priority Data
Jul. 29, 2020  (FR) ......................................  2008012

(51) Int. Cl.
*F04F 5/18*  (2006.01)
*A01H 1/02*  (2006.01)
(Continued)

(52) U.S. Cl.
CPC ............... *A01H 1/027* (2021.01); *F04F 5/18* (2013.01); *F04F 5/54* (2013.01); *F15D 1/06* (2013.01)

(58) Field of Classification Search
CPC .................. F04F 5/54; F04F 5/18; F15D 1/06
See application file for complete search history.

(56) References Cited

U.S. PATENT DOCUMENTS

2021/0045306 A1    2/2021  Baldet

FOREIGN PATENT DOCUMENTS

| DE | 102009047089 | 6/2011 |
|----|--------------|--------|
| GB | 2169192      | 7/1986 |
| GB | 2234782      | 2/1991 |

OTHER PUBLICATIONS

International Search Report dated Nov. 8, 2021.

*Primary Examiner* — P. Macade Nichols
(74) *Attorney, Agent, or Firm* — IPSILON USA, LLP

(57) ABSTRACT

The invention relates to a Coanda effect flow booster (10) for inducing a boosted flow of gas, comprising: —a main air circulation pipeline (14), —at least one injection opening that opens into the main pipeline (14), —a plurality of openings for supplying compressed motive gas, each opening configured to be connected to a source of compressed motive gas in order to supply the at least one injection opening with compressed motive gas, —at least one distribution pipeline connecting the plurality of supply openings to the at least one injection opening, —a booster profile (48) at least partially defining the at least one injection opening and forming a convex surface configured to create a Coanda effect in a flow of compressed motive gas injected through the at least one injection opening.

18 Claims, 5 Drawing Sheets

Figure 1:
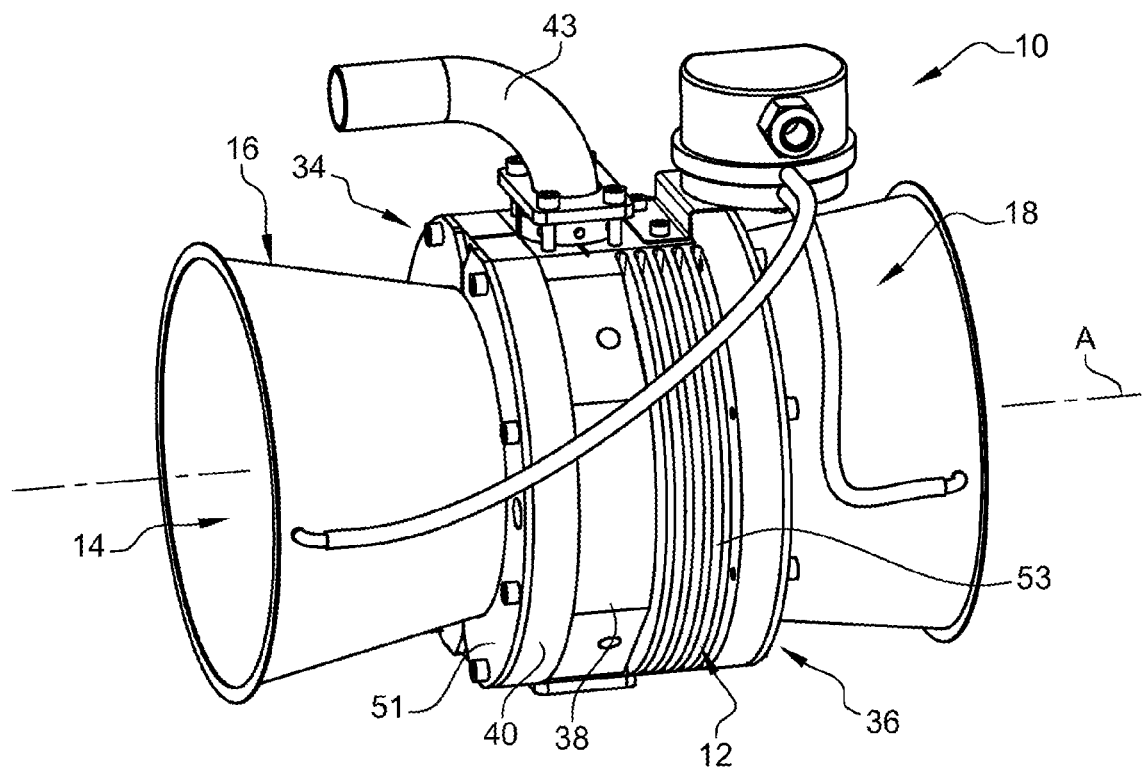

(51) Int. Cl.
*F04F 5/54* (2006.01)
*F15D 1/06* (2006.01)

COANDA EFFECT FLOW BOOSTER AND AERAULIC DEVICE COMPRISING SUCH A FLOW BOOSTER

RELATED APPLICATION

This application is a National Phase of PCT/FR2021/051400 filed on Jul. 27, 2021, which claims the benefit of priority from French Patent Application No. 20 08012, filed on Jul. 29, 2020, the entirety of which are incorporated by reference.

FIELD OF THE INVENTION

The present invention lies in the field of the amplification of the flow rate of a gas flow.

In particular, the invention relates to a Coanda effect flow amplified. Coanda effect flow amplifiers are also known as "air amplifiers" or "air movers". The invention also relates to an aeraulic device comprising such a Coanda effect flow amplifier.

PRIOR ART

A Coanda effect flow amplifier comprises in particular a main duct for circulation of a fluid, for example air. The flow amplifier makes it possible to bring about a suction flow upstream of the main duct and a blown flow downstream of this main duct. This blown flow is made up of a primary driving gas injected under pressure into the main duct and a secondary flow brought about by the Coanda effect. In particular, a specific profile of the main duct encountered by the primary driving flow makes it possible to generate a Coanda effect so as to bring about the secondary flow. This Coanda effect makes it possible to obtain a very large multiplying effect between the secondary flow brought about and the primary driving flow, in particular compared with a Venturi effect air flow generator. The primary driving flow is generally compressed air.

There exist a large number of Coanda effect air amplifiers designed to draw in gases that are clean or loaded with particles intended to be discharged as waste materials, with no consideration therefore being given to the impact of these suction devices on maintaining the integrity of very fragile particles. These commercial apparatuses, which are powered by pneumatic energy, were designed for environments exhibiting risks of inflammation in which mechanical suction devices may cause friction, heat and sparks. These air flow boosters which are used in industry are used in particular to degas the holds of merchant ships and operate at air or steam pressures that may reach 8 bar of relative pressure and bring about suction air flow speeds greater than 50 meters per second (180 km/h). The interior profiles used, which generate a negative pressure by Coanda effect have been optimized for these high pressure values and operating speeds, and the shape of these profiles is similar to that of the upper surface of high-speed aircraft wings with the side effect of fairly small ranges of speeds in optimal operation. The document GB-2234782 discloses a Coanda effect nozzle having variable suction capacities.

The operating principle of a Coanda effect flow amplifier makes it particularly predisposed for conveying very fragile particles. Specifically, a Coanda effect flow amplifier has the major advantage of exhibiting minimal obstacles in the flow cross section of the main duct, in particular compared with amplification systems comprising a fan in the through-duct or of the Venturi type, the architecture of which provides a significant reduction in the inside diameter for the passage of air and the presence in the main duct of one or more primary-air injection nozzles.

Pollen is an example of a fragile material that can be conveyed using a Coanda effect flow amplifier. In particular, pollen referred to as "recalcitrant", by analogy with the classification of seeds, is intended for almost immediate pollination since their viability is very low over time and conditional on a high hydration level. This is the case for pollen of grasses such as that of wheat (*triticum* sp.), barley (*hordeum* sp.), rice (*oryza* sp.) or maize (*Zea mays* sp.). This pollen cannot be easily preserved, is very fragile and requires a large amount of precautions for handling. Artificial pollination of plants provided with such pollen involves specific technologies and practices the respect the very brief viability of this pollen. The viability of the pollen corresponds to its reproductive potential. It is thus particularly relevant to use a Coanda effect flow amplifier to convey this type of pollen. The document FR-3078859 teaches a Coanda effect aeraulic device for pollination.

The use of known Coanda effect flow amplifiers having suction rates of less than 10 $m \cdot s^{-1}$ remains possible, but said rates are below the optimal operating ranges. The performance of the flow amplifier is thus very modest. Moreover, the driving gas inlets of the known air flow amplifiers are designed for high operating pressures with limited optimization of pressure drops, and they are also frequently tangential to the internal ring for distribution of the driving air over the Coanda profile; this results in undesirable internal turbulence of the kind that projects the drawn in particles onto the walls by centrifugation. Specifically, turbulence my occur very easily in a low pressure flow.

Moreover, it has been found that the uniformity and the stability of the flow of driving gas injected into the main duct with these known air flow amplifiers cannot be guaranteed with precision over the entire air flow cross section. This can bring about turbulence in the blown flow, which can damage the fragile materials transported, which, specifically, require a uniform and controlled blown flow.

The known air flow amplifiers are also poorly optimized in terms of mass and size. These air flow amplifiers may thus be difficult to incorporate into aeraulic systems or cause significant installation constraints.

There is therefore a need for a Coanda effect flow amplifier that does not have the abovementioned drawbacks. In particular, there is a need for a Coanda effect flow amplifier in which the aeraulic performance is improved for low conveying speeds, for example speeds lower than 10 $m \cdot s^{-1}$, so as to allow fragile materials to be conveyed.

OBJECTS AND SUMMARY

To that end, the invention relates to a Coanda effect flow amplifier for bringing about an amplified air flow, having:

- a main air circulation duct,
- at least one injection orifice opening into the main duct,
- a plurality of orifices for feeding compressed driving gas, each being configured to be connected to a source of compressed driving gas in order to feed said at least one injection orifice with compressed driving gas,
- at least one distribution duct connecting said plurality of feed orifices to said at least one injection orifice,
- an amplification profile at least partially delimiting said at least one injection orifice and forming a convex surface configured to bring about a Coanda effect in a flow of compressed driving gas injected through said at least one injection orifice.

The use of a Coanda effect flow amplifier having a plurality of feed orifices allow improved distribution of the driving gas inside the distribution duct and through the injection orifice or orifices. The flow of driving gas injected into the main duct is thus more uniform and more stable than in a known configuration of a Coanda effect flow amplifier having only one feed orifice. For example, the presence of at least two feed orifices of the amplifier allows a significant improvement, by at least 25%, in terms of compressed air flow rate in the amplifier, and drawn into and blown in the main duct.

The known Coanda effect air flow amplifiers generally have a distribution duct in the form of an annular cavity. The feeding of this annular cavity with driving gas tends to generate turbulence on account of the geometry of this cavity. The use of a plurality of feed orifices makes it possible to mix the flows of driving gas and to smooth them in order to feed the injection orifice or orifices with a flow of driving gas that is as uniform as possible.

The term "uniform" is understood to mean a flow that is a laminar as possible. In particular, the speed of the driving gas through the plurality of injection orifices is substantially identical at a given time. The expression "substantially identical" is understood to mean that these driving gas speeds are contained in a range lower than or equal to 2 $m \cdot s^{-1}$, preferably lower than or equal to 1 $m \cdot s^{-1}$. This uniform nature applies to a given distribution duct. If the flow amplifier comprises a plurality of distribution ducts, each distribution duct has a uniform driving gas flow.

Moreover, this configuration in which the flow amplifier comprises a plurality of feed orifices makes it possible to envision segmentation of the feed of driving gas so as to obtain speeds that are deliberately different depending on the injection orifices.

According to one embodiment of the flow amplifier, the main air circulation duct extends along a circulation axis, said at least one distribution duct forming an annular distribution cavity extending along and around the circulation axis, said at least one injection orifice forming a slot extending at least partially around the circulation axis.

For example, a radial dimension of the slot may be limited by the presence of a connecting radius exhibited by a deflecting wall facing each of the feed orifices, this deflecting wall being adjacent to the slot opening onto the injection orifice.

This slot may be formed continuously as a single slot or discontinuously with a plurality of slot portions. It is thus possible to form a slot that is subsequently segmented by partition elements in order to obtain these slot portions.

According to one embodiment of the flow amplifier, said at least one injection orifice is formed by an annular injection cavity extending around the circulation axis and radially with respect to this circulation axis.

The injection cavity thus forms a disk, the internal end of which leads into the interior of the main duct and the opposite end of which communicates with said at least one distribution duct.

According to one embodiment of the flow amplifier, the feed orifices are oriented transversely to the circulation axis, the flow amplifier also comprising at least one deflecting wall facing each of the feed orifices.

The transverse orientation of the feed orifices combined with the presence of a deflecting wall makes it possible to smooth the flow of driving gas feeding the distribution duct. This smoothing makes it possible to stabilize the flow of driving gas before it reaches the plurality of injection orifices. According to one particular configuration, the feed orifices are oriented radially with respect to the circulation axis.

According to one embodiment of the flow amplifier, said flow amplifier comprises a plurality of mutually independent distribution ducts and a plurality of injection orifices, each distribution duct extending between at least one of the plurality of feed orifices and at least one of the plurality of injection orifices so that it is possible to inject separate flows of compressed driving gas through the plurality of injection orifices.

The independence of the distribution ducts makes it possible to form separate distribution lines that lead to separate injection orifices. It is thus possible to inject separate flows of driving gas, the physical or physico-chemical properties of which are different. Specifically, it is possible to inject flows of driving gas with different speeds or different gas types.

According to one embodiment of the flow amplifier, said plurality of distribution ducts is formed by the annular distribution cavity, the flow amplifier also comprising at least two partition elements for compartmentalizing the distribution cavity so as to form at least two independent distribution ducts.

According to one embodiment of the flow amplifier, said flow amplifier also comprises means for adjusting a flow cross section for the driving gas of said at least one injection orifice so as to regulate the flow rate of driving gas ultimately passing through said at least one injection orifice.

According to one embodiment of the flow amplifier, the adjusting means are configured to separately adjust the flow cross section for driving gas of at least two injection orifices communicating with independent distribution ducts so that it is possible to inject flows of compressed driving gas with different flow rates through said at least two orifices.

According to one embodiment of the flow amplifier, the plurality of injection orifices comprises at least one first and at least one second injection orifice, which are intended to be disposed respectively in the lower part and in the upper part of the main air circulation duct so that it is possible to bring about a different amplified air flow rate in the lower and upper parts.

According to one embodiment of the flow amplifier, the adjusting means are configured to separately adjust the flow cross section for driving gas of at least four injection orifices communicating with independent distribution ducts, the plurality of injection orifices also comprising at least one third and at least one fourth injection orifice, which are intended to be disposed respectively at opposite lateral parts of the main air circulation duct.

According to one embodiment of the flow amplifier, said flow amplifier comprises:
  a body in which said main air circulation duct, the plurality of feed orifices, said at least one distribution duct, the amplification profile and a first portion of said at least one injection orifice are formed,
  an injection ring forming a second portion of said at least one injection orifice, the injection ring being configured to be disposed facing the body, the first and second portions of said at least one injection orifice facing one another, the distance between the first and second portions of said at least one injection orifice defining a flow cross section for driving gas through said at least one injection orifice.

According to one embodiment of the flow amplifier, the adjusting means are configured to adjust the distance between the injection ring and the body so as to vary the flow cross section for driving gas of said at least one injection orifice.

According to one embodiment of the flow amplifier, the ring is movable with respect to the body about at least one axis transverse to a circulation axis of the main circulation duct, the adjusting means being configured to adjust the inclination angle of the ring with respect to said at least one transverse axis so as to vary the flow cross section for driving gas of said at least one injection orifice asymmetrically.

The invention also relates to an aeraulic apparatus for pollinating at least one receiver plant with pollen collected from at least one donor plant, comprising:
  a member for collecting the pollen from said at least one donor plant,
- a member for diffusing the pollen over at least one receiver plant,
- a channel for conveying the pollen collected from the collecting member to the diffusing member or members, and at least one flow amplifier as described above.

The invention also relates to the use of a flow amplifier as described above to amplify an air flow comprising particles exhibiting a predetermined sedimentation rate, wherein the Coanda effect flow amplifier brings about an air flow inside the main circulation duct, the speed of which is higher than the predetermined sedimentation rate.

According to one embodiment of the use of the flow amplifier, the speed of the air flow brought about inside the main circulation duct is less than or equal to 10 $m \cdot s^{-1}$, preferably less than or equal to 5 $m \cdot s^{-1}$.

BRIEF DESCRIPTION OF THE DRAWINGS

The appended drawings illustrate the invention:

FIG. 1 shows a perspective view of a Coanda effect flow amplifier according to the invention.

FIG. 2 shows a schematic view in section of a schematic diagram of the Coanda effect flow amplifier in FIG. 1, in which a suction flow, a blown flow and a flow of driving gas are illustrated.

FIG. 3 shows a view in cross section of the flow amplifier in FIG. 1.

FIG. 4 shows a detailed view of FIG. 3.

FIG. 5 shows a perspective view of a main body of the flow amplifier in FIG. 1.

FIG. 6 shows an exploded view of the flow amplifier in FIG. 1.

FIG. 7 shows a set of two elements for reducing the section of the distribution duct for primary driving air belonging to an amplification kit that also comprises the flow amplifier in FIG. 1.

FIG. 8*a* and FIG. 8*b* show detailed views of embodiment variants of the detailed view in FIG. 4.

DESCRIPTION OF EMBODIMENT(S)

With reference to FIG. 1, a Coanda effect flow amplifier 10 comprises an amplifier body 12 defining a main air circulation duct 14 extending along a circulation axis A. For the sake of clarity, the Coanda effect flow amplifier 10 will be referred to as "flow amplifier 10" below. The main duct 14 has for example a length of several meters, and the flow amplifier 10 is positioned more than one meter away from an inlet and from an outlet of this main duct 14.

The flow amplifier 10 also comprises an upstream connector 16 and a downstream connector 18 which are connected respectively to a first end 34 and a second end 36 of the amplifier body 12. The first end 34 and second end 36 are disposed at opposite ends along the circulation axis A. The upstream connector 16 and downstream connector 18 are configured to connect the flow amplifier 10 to aeraulic pipes. Preferably, these aeraulic pipes are standard. By way of example, a standard pipe has an inside diameter of 200 mm for an application to the conveying of pollen.

The upstream connector 16 and downstream connector 18 have a conical section in a plane perpendicular to the circulation axis A. The upstream connector 16 and downstream connector 18 each comprise a proximal end intended to be fixed to the amplifier body 12 and a distal end intended to be fixed to a standard aeraulic pipe. The smallest section of the upstream connector 16 and downstream connector 18 is disposed at their proximal end, which is intended to be fixed to the amplifier body 12. The diameter of the main duct 14 is thus smaller than the diameters of the aeraulic ducts to which the upstream connector 16 and downstream connector 18 are intended to be connected.

The amplifier body 12 comprises a main body 38 forming the main duct 14 within it. The main duct 38 forms a ring of annular section, the internal wall of which forms the main duct 14. In particular, the main body 38 forms an annular section about the circulation axis A. The amplifier body 12 also comprises an injection ring 40 disposed against the main body 38 along the circulation axis A.

With reference to FIGS. 2 to 4, the flow amplifier 10 comprises an injection circuit 19 for injecting driving gas into the main duct 14. This injection circuit 19 is preferably formed at least partially, more preferably entirely, inside the amplifier body 12. According to a preferred embodiment, the injection circuit 19 is formed at least partially inside the main body 38.

With reference to FIG. 2, which illustrates a schematic diagram of the flow amplifier 10, a blown flow 32 is brought about by the flow amplifier 10, combining a flow of driving gas 30 coming from the injection circuit 19 and a secondary suction flow 28. The flow of primary driving gas 30 is annular and disposed at the periphery of the main duct 14 with respect to the circulation axis A, in contact with the walls of the main duct 14. The secondary suction flow 28 is central with respect to the circulation axis A and exhibits a lower velocity than the flow of primary driving gas 30. Thus, this injection of a flow of primary driving gas 30 in an annular form makes it possible to expose the fragile materials conveyed essentially to the central zone with the secondary suction flow 28 of lower velocity. The flow amplifier 10 is configured to bring about, from the injection circuit 19, the secondary suction flow 28 with a predetermined speed, wherein the ratio between said secondary suction flow 28 in the main duct 14 and the flow of primary driving gas 30 is greater than or equal to 10, preferably greater than or equal to 15, even more preferably greater than or equal to 17. Thus, when the ratio between said secondary suction flow 28 in the conveying channel 16 and the flow of primary driving gas 30 is equal to 17, the quantity of primary driving gas 30 is approximately equal to 6% of the downstream blown flow 32. The rate of driving gas injected is very important for the transport of fragile particles since it increases the differential between the suction rate that is intended to be optimized and the blowing rate, which should not be increased too much so as not to damage the particles transported. Energy optimization is also an expected result of the matching of the amplification profiles to the transport speeds desired.

The injection circuit 19 comprises a plurality of orifices 42 for feeding compressed driving gas, at least one injection orifice 44 opening into the main duct 14 and a distribution duct 46 placing the plurality of feed orifices 42 into fluidic communication with the injection orifice or orifices 44. Preferably, the injection circuit 19 has only one injection orifice 44 when it comprises one distribution circuit 46. More preferably, the injection circuit 19 comprises a number of injection orifices 44 equal to the number of distribution ducts 46.

The feed orifices 42 are configured to be connected to a source of compressed driving gas 24 so as to allow the injection of compressed driving gas into the distribution duct 46 in order to subsequently be injected into the main duct 14 through the injection orifices 42. The feed orifices 42 are in particular configured to be connected to a feed line 43 in fluidic communication with the source of compressed gas 24.

This source of compressed gas 24 can be integrated into the flow amplifier 10 or be connected thereto. The source of compressed gas 24 may be in the form of a compressor connected to a gas tank for compressing it and injecting it into the injection circuit 19. This is gas is preferably ambient air.

The feed orifices 42 are formed on an outer wall of the main body 38. The feed orifices 42 are preferably oriented radially with respect to the circulation axis A in order to avoid any phenomenon of turbulence within the injection circuit 19 and in the main duct 14. Specifically, a tangential orientation of the feed orifices 42 would tend to generate turbulence and swirl, which would have a detrimental effect on the uniformity and the stability of the flow of driving gas. As indicated above, this turbulence could have a negative effect on the integrity of the fragile material transported.

The feed orifices 42 are formed around the circulation axis A. Preferably, the feed orifices 42 are distributed regularly about the circulation axis A on the outer wall of the main body 38 so as to distribute the flow of driving gas in the distribution duct 46. The expression "distributed regularly" is understood to mean that the angular sector separating two adjacent feed orifices 42 is equal to 360° divided by the total number of feed orifices 42. Thus, if the main body 38 comprises two feed orifices 42, these will be separated by an angle of 180°. The main body 38 may comprise at least three, at least four or even at least five feed orifices 42.

The feed orifices 42 are preferably not aligned with the one or more injection orifices 44 so as to prevent the feeding of driving gas from a feed orifice 42 to an injection orifice along a continuous straight trajectory. In other words, a feed orifice 42 is not positioned facing an injection orifice 44 in order to avoid direct access of the gas from the feed orifice 42 to the injection orifice 44. Thus, the feed orifices 42 and the at least one injection orifice 44 are preferably offset along the circulation axis A or offset angularly about the circulation axis A. Thus, the distribution duct 46 forms a deflecting wall facing each of the feed orifices 42. The flow of driving gas thus meets this deflecting wall from the outlet of a feed orifice and is stabilized in the distribution duct 46 before being injected through one or more injection orifices 44.

Figure 2:
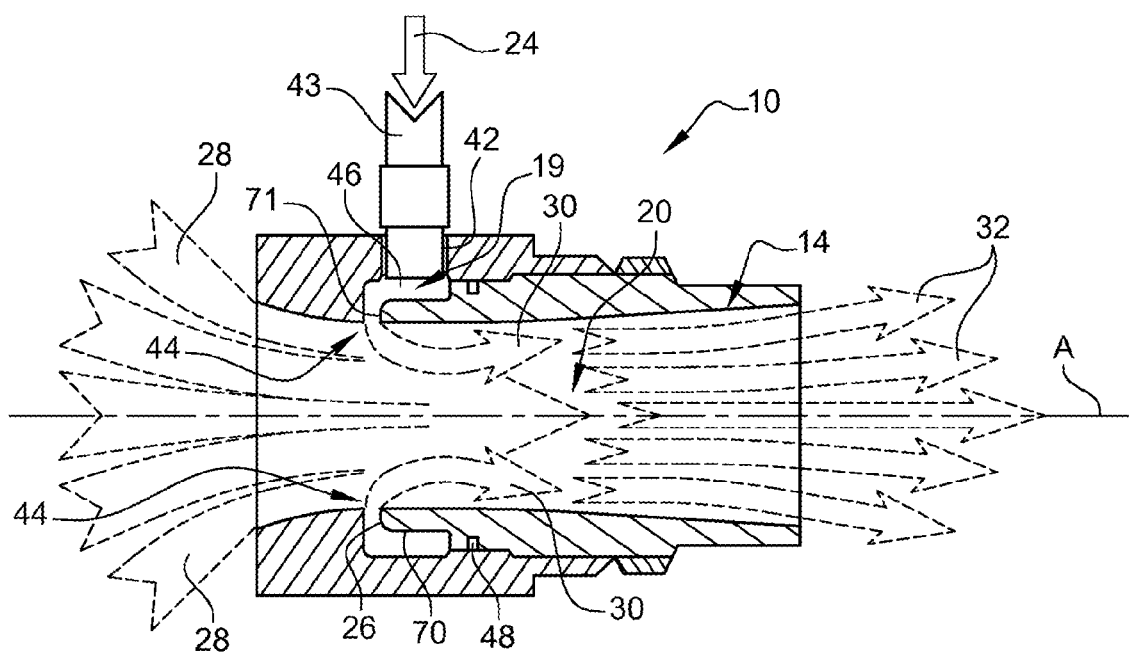
Figure 3:
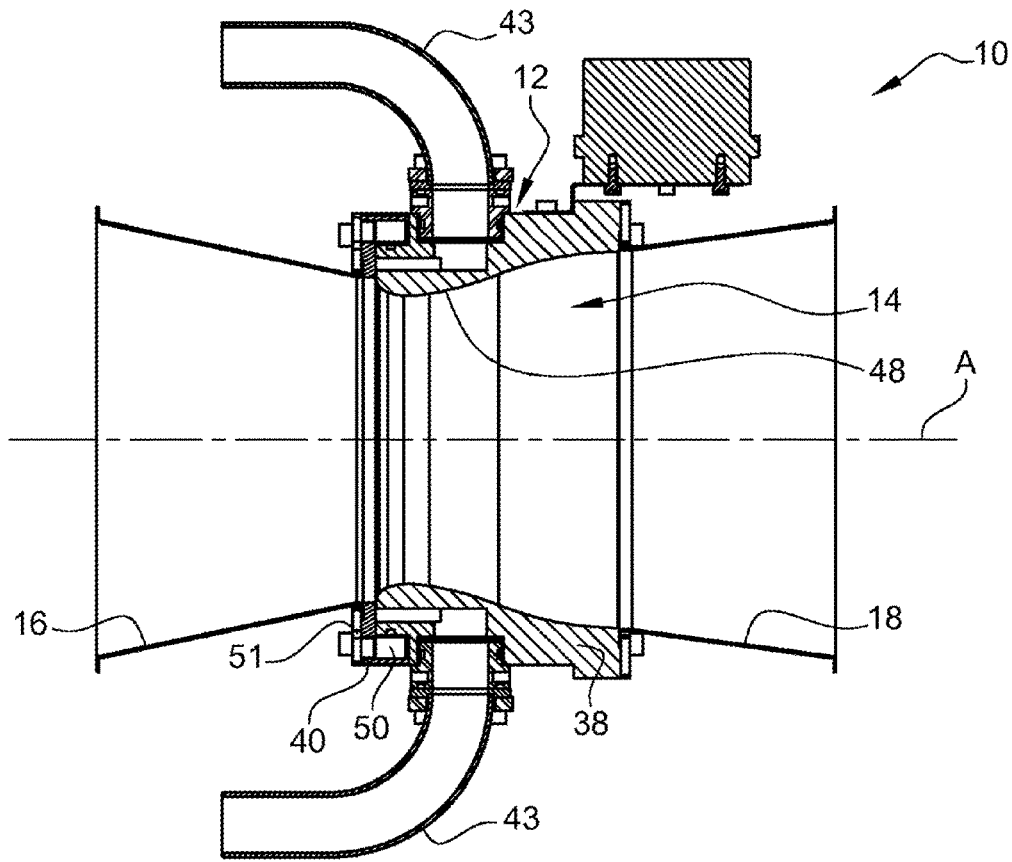
Figure 4:
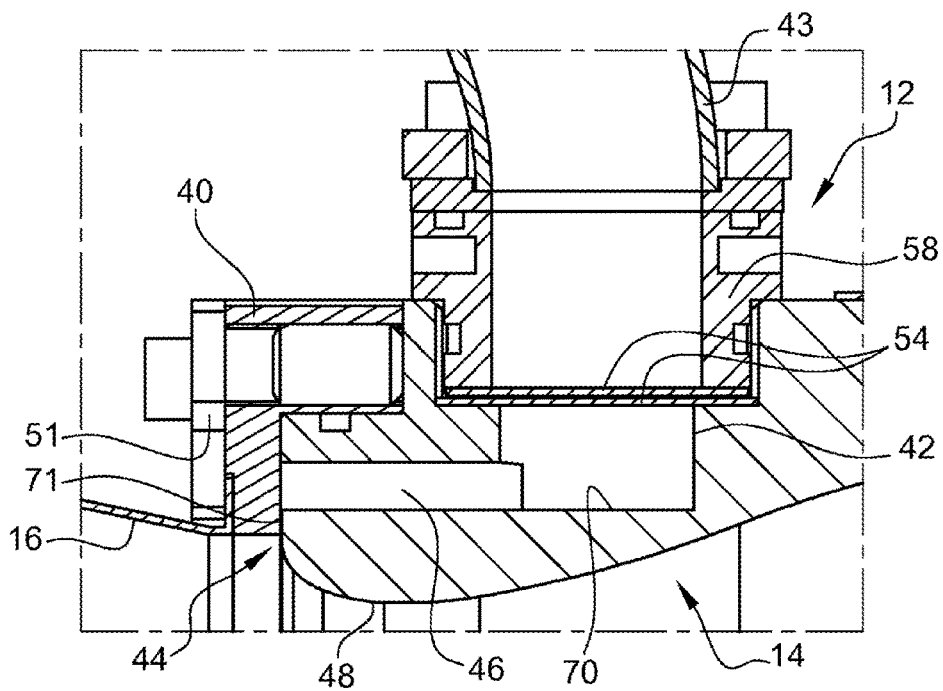

According to a preferred configuration that can be seen in FIGS. 2 to 4, the distribution duct 46 extends at least partially along the circulation axis A. The feed orifices 42 and the at least one injection orifice 44 are offset along the circulation axis A so as to extend in planes perpendicular to the circulation axis A that are different from one another.

The distribution duct 46 preferably forms an annular distribution cavity extending along and around the circulation axis A.

The injection orifice 44 is preferably made in the form of a slot 71 extending at least partially around the circulation axis A. The slot extends preferably along an angular sector about the circulation axis A. Even more preferably, the slot 71 is circular and forms an annular orifice extending around the circulation axis A. Thus, the driving gas is injected through the slot in the form of an annular air knife about the circulation axis A, at the periphery of the main duct 14. The slot 71 may be continuous all around the circulation axis A. Alternatively, the slot 71 may be formed discontinuously by a plurality of openings or of portions of slots in order in this way to form a plurality of injection orifices 44.

As can be seen in the views in section in FIGS. 2, 4, 8*a* and 8*b*, the slot 71 has a radial dimension relative to the axis A, such that it is possible to determine both a radial height 73 of this slot and an axial width 74 of the slot along the axis A. The axial height of the slot 71 which opens through the injection orifice 44 corresponds to the height where the slot has the same axial width 74. In the embodiments in FIGS. 2 and 4, the slot is radially higher than that in the embodiments in FIGS. 8*a* and 8*b*. Specifically, in the embodiments in FIGS. 8*a* and 8*b*, the radial height 73 of this slot 71 is limited by the presence of a connecting radius 72 defined between an edge of the slot and a deflecting wall 70. This deflecting wall 70 faces each of the feed orifices 42 and is adjacent to the slot 71. This connecting radius is for example around 0.5 to 3 mm, advantageously between 1 and 2 mm.

Figure 8A:
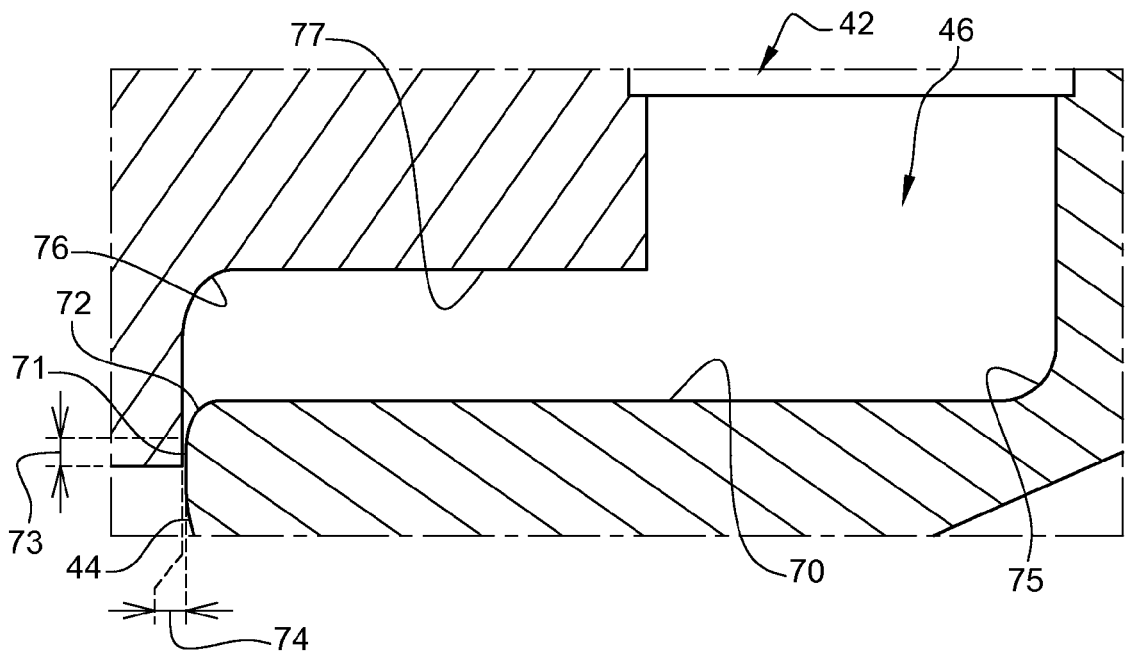
Figure 8B:
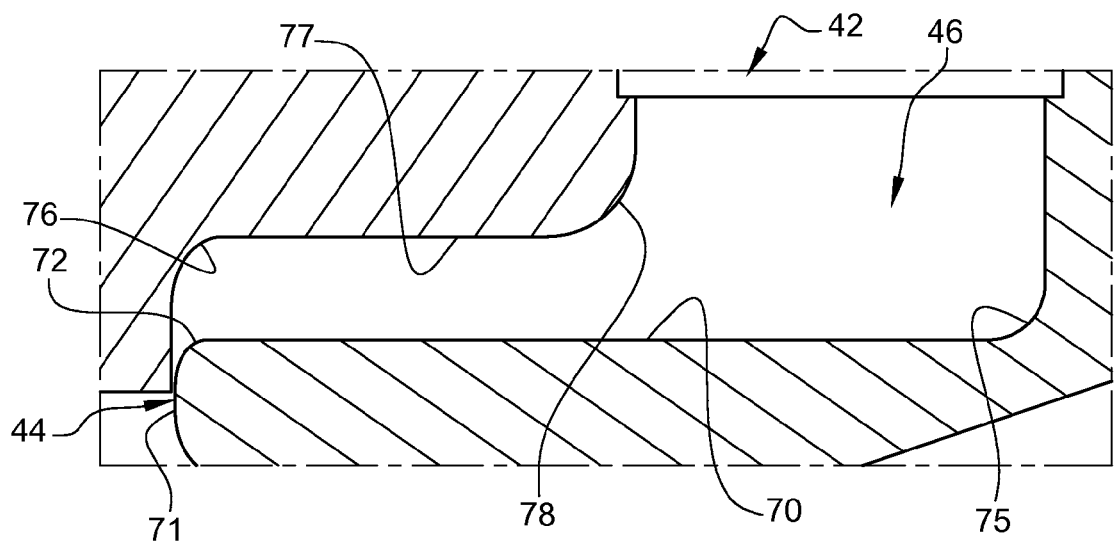

As can also be seen in FIGS. 8*a* and 8*b*, other edge fillets and connecting radii can be provided in the distribution duct 46. For example, an edge fillet 75 may be provided adjacent to the deflecting wall 70 and facing the feed orifice 42. Another edge fillet 76 may be provided in the wall 77 of the amplifier body 12 which faces the slot 71, the wall 77 and the deflecting wall 70 together defining at least one section of the distribution duct 46. Another connecting fillet 78, in FIG. 8*b*, can also be provided to soften the junction between the section defined between the walls 77 and 70 and an adjacent and transverse section in communication with the feed orifice or orifices. The edge fillets 75, 76 or connecting fillet 78 may measure between 1 and 5 mm, preferably around 3 mm.

Surprisingly, it has been found that the double feed significantly increases the suction rate, at the inlet of the main duct 14, and the blowing speed at the outlet of the main duct 14. Moreover, the internal structural modifications of the distribution duct, through the presence of these connecting fillets and edge fillets further improves the performance in terms of speed/rate, and therefore the flow rate of pollen picked up and distributed in a single operation.

The section of the slot along the circulation axis A may be constant around the entire circumference of the main duct 14 so as to bring about an air flow that is identical around the entire perimeter of the flow amplifier 10. In other words, the section of the slot may be symmetric about the circulation axis A. Alternatively, the section of the slot may be variable about the circulation axis A in order to bring about a flow of secondary gas having a speed that varies about the circulation axis A. The section of the slot may thus be asymmetric. This variation in the flow of secondary gas is particularly advantageous for limiting the natural propensity of pollen to settle under the effect of gravity and therefore to improve the keeping of the pollen in suspension. To that end, the section of the slot is preferably larger in its upper part than in its lower part. In other words, the slot has an upper portion have a section larger than the section of a lower portion disposed at the opposite end from the upper portion. This variable configuration of the section of the slot makes it possible to bring about a more intense negative pressure in the upper portion.

The main body 38 also comprises an amplification profile 48 at least partially delimiting the injection orifice 44. The amplification profile 48 forms a convex surface configured to bring about a Coanda effect in the flow of compressed driving gas 30 injected through said injection orifice 44.

The amplification profile 48 is disposed downstream in contact with the injection orifice 44 with respect to the direction of movement of the gases and materials conveyed in the main duct 14. The amplification profile 48 may be obtained via a curved surface so as to optimize the Coanda effect. Alternatively, the amplification profile 48 may be obtained via a plurality of straight segments so as to make it easier to manufacture.

The amplification profile 48, when it is seen in cross section, preferably corresponds to a portion of a "NACA" profile used in aeronautical construction, in particular the upper half of the "NACA" profile. Thus, the amplification profile 48 corresponds preferably to a leading edge disposed at the injection orifice 44, an upper surface and a trailing edge in the direction of the second end 36 of the main body 38. By way of example, the amplification profile 48 may correspond to an upper half of a "NACA0030" profile comprising camber of the reference line (from the leading edge to the trailing edge) of 0 degree, a camber position of 0% and a profile thickness of 30% of the chord, i.e. of the distance between the leading edge and the trailing edge.

The Coanda effect is the property of a flow of gas or liquid to follow an adjacent curved contour such as the amplification profile 48 without coming away therefrom. In a Coanda effect flow amplifier, the flow of primary driving air adheres to the curved surface in the form of a thin layer of air at high speed, which is accompanied by a negative pressure zone, thereby causing the ambient air to be driven at a very high multiplying rate. The amplification profile 48 is configured so as to make the Coanda effect last along the greatest length possible in order to maximize the total area of the primary air flow at high speed with the side effect of driving secondary air at a very high rate that explains the flow amplifying nature of such a device.

According to a preferred configuration illustrated in FIGS. 3 and 4, the injection orifice 44 is delimited by two lateral walls formed respectively by the main body 38 and the injection ring 40. In other words, the injection orifice is formed by a space formed between the main body 38 and the injection ring 40. Thus, an end wall of the main body 38, for the one part, and an end wall of the injection ring 40, for the other part, form the injection orifice 44. This arrangement makes it possible to obtain an injection orifice 44, the dimension of which along the circulation axis A can be precisely calibrated.

In this preferred configuration, the distribution duct 46 opens out at this lateral wall of the main body 38. The injection ring 40 is shaped so as to close the end opening into the distribution duct 46 when the injection ring 40 is disposed against the main body 38. One or both of the main body 38 and the injection ring 40 are shaped so as to maintain a space corresponding to the width of the injection orifice 44 along the circulation axis A when they are placed in contact with one another.

The flow amplifier 10 preferably comprises means for adjusting the flow cross section of the injection orifice 44, or at least a portion of the plurality of injection orifices 44, so as to regulate the flow rate of driving gas passing through said injection orifice or orifices 44.

In the configuration in FIGS. 3 and 4, the adjusting means are configured to adjust the distance between the injection ring 40 and the main body 38 so as to vary the flow cross section for driving gas of said injection orifice 44 or of at least one of the injection orifices 44. The injection ring 40 is thus movable with respect to the main body 38 about at least one axis transverse to the circulation axis A of the main duct 14. The adjusting means are configured for example to adjust the inclination angle of the injection ring 40 with respect to said at least one transverse axis so as to vary the flow cross section for driving gas or the injection orifice or orifices 44 asymmetrically.

In practice, the rotation of the injection ring 40 varies the distance between the main body 38 and the injection ring 40 over an angular sector of the injection orifice 44 or of the plurality of injection orifices 44. This variation in distance brings about a variation in the flow cross section for the driving gas through this angular sector and thus makes it possible the vary the flow rate thereof through this angular sector. The asymmetry brought about by the angular position of the injection ring 40 thus makes it possible to obtain an asymmetric flow rate about the circulation axis A. It is thus possible to increase the flow rate of driving gas in the upper part of the flow amplifier 10 in order to compensate for the effect of gravity on the materials conveyed in order to limit any contact between the fragile materials and the walls of the main duct 14.

In order to compensate for gravity, the asymmetry generated by the injection ring 40 is realized by moving the ring about a substantially horizontal axis. Alternatively or in addition, it is also possible to move the injection ring 40 along a substantially vertical axis so as to generate an asymmetry between lateral angular sectors. This lateral asymmetry could make it possible for example to shift the particles transported toward one side of the main duct 14 in order to avoid an obstacle or to anticipate a bend or a fork in this duct downstream of the flow amplifier 10 in order to limit the risks of collision.

The adjusting means for moving the injection ring 40 comprise for example a plurality of adjusting screws 50 that bear on the main body 38 in order to adjust the spacing between the injection ring 40 and the main body 38. These adjusting screws 50 are screwed into the injection ring 40. The injection ring 40 is prevented from moving between the flanges 51 and the main body 38 via screws. The withdrawal and asymmetric bearing of the adjusting screws 50 between several angular sectors of the injection ring 40 makes it possible to vary the distance between the injection ring 40 and the main body 38 asymmetrically.

According to a preferred embodiment, the injection circuit 19 comprises a plurality of distribution lines that are independent of one another as far as the injection of the driving gas into the main duct 14. In this case, the flow amplifier 10 comprises a plurality of distribution ducts 46 that are independent of one another. The flow amplifier 10 also comprises a plurality of injection orifices 44. Each feed orifice 42 and each injection orifice 44 belongs to a distribution line such that they are in fluidic communication only with one distribution duct.

These independent distribution lines make it possible to form independent flows of driving gas. It is thus possible to supply flows of driving gas having different characteristics, such as a different pressure of the gas or a different type of driving gas. Specifically, it could be envisioned to mix a single flow of driving gas with an additive in order to provide specific characteristics in an angular sector of the main duct 14. It is also possible to supply flows of gas having different pressures that bring about different injection flow rates around the circulation axis A. These separate distribution lines also allow the installation of a measurement device, for example for the pressure of the gas, or of safety devices.

Figure 5:
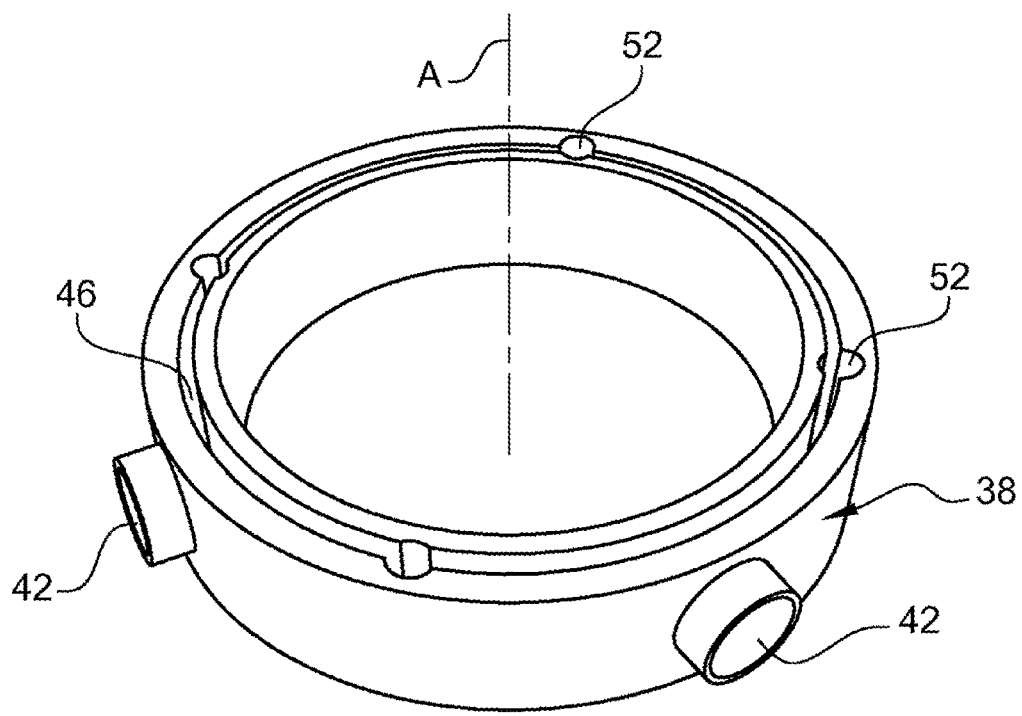
Figure 7:
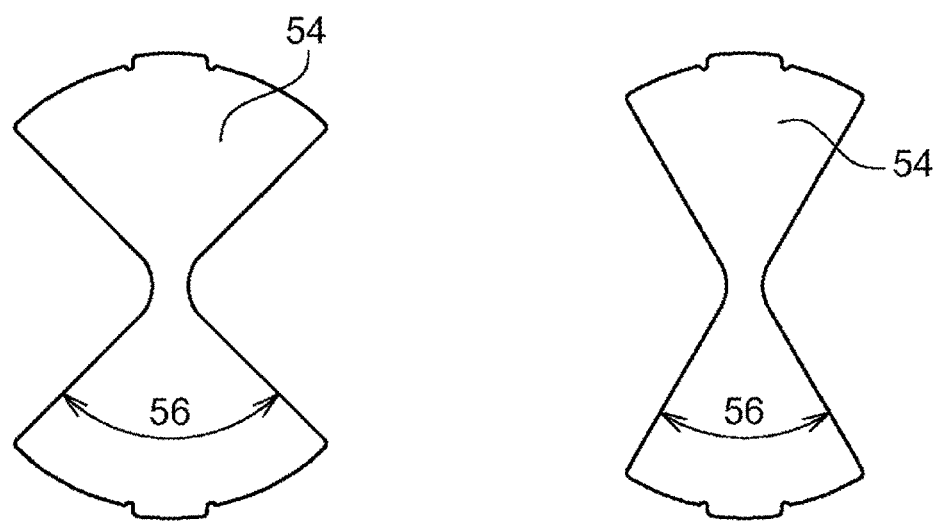

With reference to FIG. 5, the independent distribution ducts 46 may be formed by inserting partition element 52 into an annular cavity. The distribution ducts 46 are thus portions of an annular cavity. These partition elements 52 extend along the circulation axis A so as to define distribution ducts 46 extending along the circulation axis A. In addition, the partition elements 52 may be shaped to separate the plurality of injection orifices 44 into angular sectors corresponding to the different distribution ducts 46. The partition elements 52 are preferably disposed inside this annular cavity so as to segment the annular cavity into angular sectors that communicate at one end with a feed orifice 42 and at an opposite end with one or more injection orifices 44. The flow amplifier 10 preferably comprises as many feed orifices 42 as distribution ducts 46. Thus, each feed orifice 42 is preferably in fluidic communication with one distribution duct 46.

The partition elements 52 are for example cylinders, made for example of elastic material, which are disposed between the concentric walls forming the annular cavity. These cylinders are preferably housed inside housings formed in the walls of the annular cavity. The partition elements 52 extend preferably beyond the lateral wall of the main body 38 so as to bring about axial and radial compression of said partition elements 52 in order to improve the sealing between distribution lines.

In a similar manner to the adjustment of the flow cross section of the injection orifices 44 via the adjusting means, the distribution lines may be distributed around the circulation axis so as to define angular sectors about the circulation axis A in order for it to be possible to compensate for gravity or to shift the particles conveyed toward a portion of the main duct 14 in order to anticipate for example a change in direction or a fork. Alternatively, it is possible to define zones through which particles of different types are conveyed. It is thus possible to convey a first type of material in the lower and upper angular sectors and a second type of material in the lateral angular sectors. The creation of a stable blown flow makes it possible to avoid any exchanges of material between these angular sectors.

The main body 38 may also have external reliefs for optimizing the thermal stability of the flow amplifier 10, making it possible to prevent the formation of condensates inside the main duct 14 and in particular at the injection orifices 44 for the primary driving gas, which brings about, through the partial expansion of the compressed gas, an endothermal reaction. Specifically, the presence of condensates on walls that have been excessively cooled is highly prejudicial to the conveying of fragile material such as pollen. These condensates could soil the interior of the main duct 14 and cause pollen to adhere or clump such that the reproductive potential of the pollen is reduced.

These reliefs may be made in the form of fins 53 provided on the outer wall of the main body 38. These reliefs or fins 53 make it possible to increase the surface areas for heat exchange with the ambient air so as to prevent the appearance of condensates as a result of the expansion of the primary driving gases.

The flow amplifier 10 is preferably made of cast aluminum, the good thermal conductivity of which makes it possible to avoid the cold spots that bring about condensation. Preferably, the flow amplifier 10 is made of a material having a thermal conductivity greater than or equal to 150 $W \cdot m^{-1} \cdot K^{-1}$.

According to one embodiment, the flow amplifier 10 may also comprise means for varying the gas flow rate through the injection circuit 19. These means for varying the gas flow rate may be configured to vary the pressure of the driving gas within the distribution lines or to vary the flow cross section for the gas at the feed orifices 42. This second alternative is illustrated for example in FIGS. 4, 6 and 7, in which the means for varying the gas flow rate comprise at least one section reducing element 54 disposed through a feed orifice 42. This section reducing element 54 has a lateral wall intended to act as an obstacle to the flow of driving gas passing through the feed orifice 42. This lateral wall of the section reducing element 54 is calibrated such that the flow cross section that remains available for the passage of the driving gas is known. This section reducing element 54 is integrated removably into the feed orifice 42 so as to make it possible to choose the pressure drop undergone by the driving gas and therefore the flow rate at which it flows through the feed orifice 42. Preferably, the flow amplifier 10 belongs to a flow amplification kit comprising the flow amplifier 10 and a second of section reducing elements 54 having calibrated and different obstruction sections. The user can thus choose to place differently calibrated section reducing elements 54 through the feed orifices 42 in order to achieve different flow rates in the distribution lines.

With reference to FIG. 7, the section reducing element 54 may be in the form of a throttle valve comprising a central part and two angular sectors extending in opposite directions from this central portion. The angular dimension 56 of each of the angular sectors is then predetermined to correspond to a certain level of reduction in section. By way of example, the section reducing element 54 disposed on the left in FIG. 7 has an angular dimension 56 equal to 60°. Similarly, the section reducing element 54 disposed on the right in FIG. 7 has an angular dimension 56 equal to 90°.

According to a preferred configuration illustrated in FIGS. 3 and 4, the variation means use a combination of two section reducing elements 54 that are superposed on one another through the feed orifice 42. These two section reducing elements 54 are rotatable with respect to one another so that it is possible to vary the flow cross section available for the driving gas. By way of example, a first section reducing element 54 is secured to the main body 38 and a second section reducing element 54 is secured to a rotatable part, in this case an adjusting ring 58. Thus, the adjusting ring 58 is mounted so as to be able to be rotatable with respect to the main body 38. Thus, a rotation of the adjusting ring 38 allows the second section reducing element 54 to rotate and therefore allows a variation in the flow cross section available for the driving gas. The flow rate adjusting ring 58 is disposed between the feed line 43 and the main body 38.

This configuration using a plurality of section reducing elements 54 allows continuous adjustment of the flow rate of driving gas passing through the feed orifice 42. This adjustment is thus more flexible and more precise. Specifically, the adjustment of the flow rates of driving gas at low pressures is very sensitive and requires a continuous adjusting device in order to be entirely satisfactory. The adoption of a complete set of section reducing elements 54, for example with an angle 56 of 30, 60 and 90°, allows a range of obstruction of the distribution duct 46 from 60° through the adoption of a set of 30° section reducing elements 54 that are precisely aligned and/or superposed and up to complete 360° closure if necessary through the use of a set of two 90° section reducing elements 54 offset by 90°.

Figure 6:
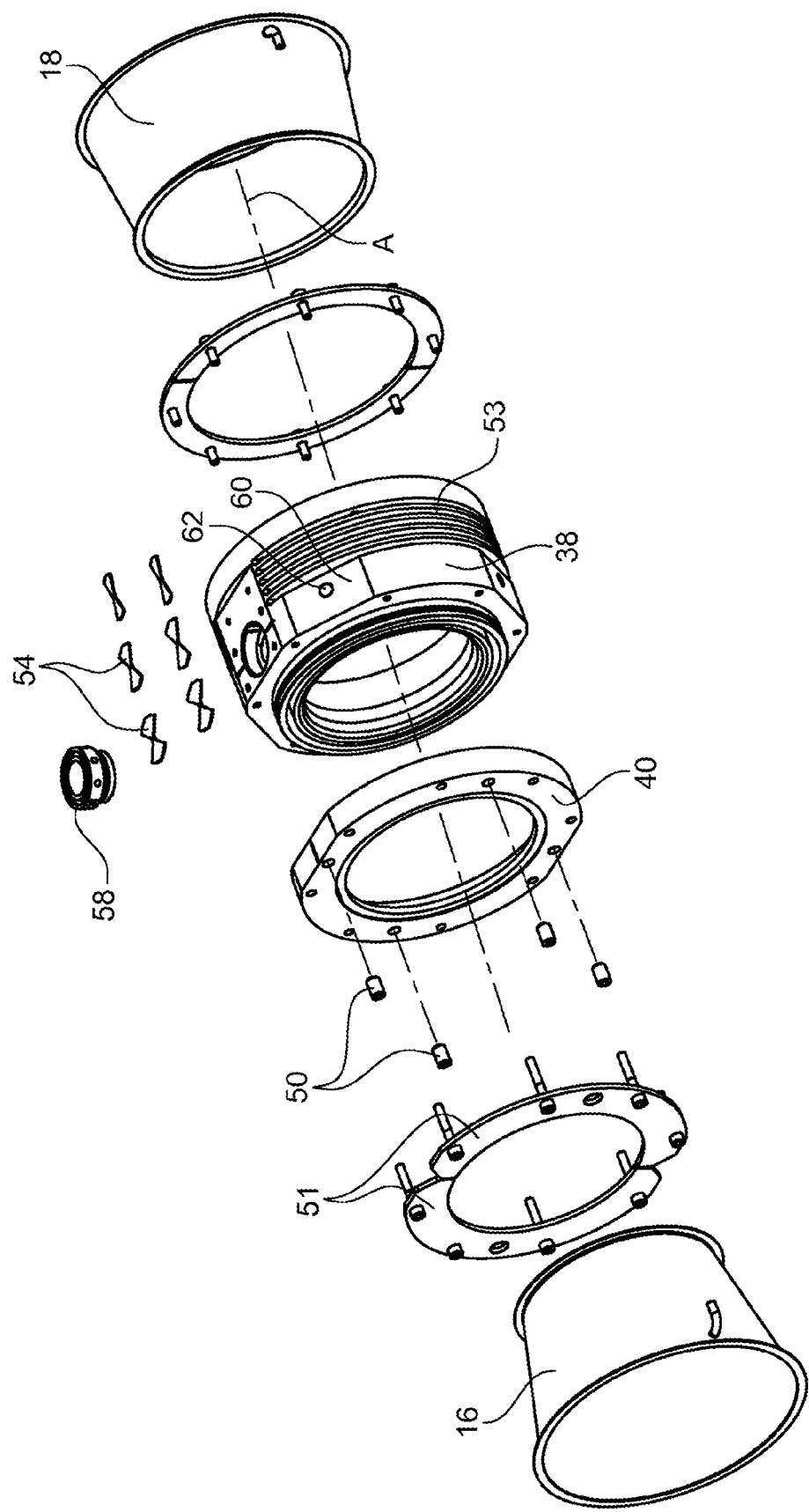

With reference to FIG. 6, the main body 38 may also have at least one flat contact surface 60 formed by its outer wall. This contact surface 60 allows the integration of the flow amplifier 10 within an aeraulic device. A blind drilled hole 62 may thus be provided close to or at this contact surface 60 in order to fix the flow amplifier to a structure. This contact surface 60 makes it possible to avoid the use of interface parts which would make the aeraulic device heavier. The contact surface 60 also allows better electrical continuity with the structure so as to discharge the static electricity generated by the triboelectric friction of the conveyed materials.

Also proposed is an aeraulic apparatus comprising a flow regulator 10 as described above, an upstream pipe for connecting to the upstream connector 16 and a downstream pipe for connecting to the downstream connector 18 of the flow amplifier 10.

The aeraulic appliance is for example an aeraulic appliance for the pollination of at least one receiver plant with pollen collected from at least one donor plant. The aeraulic appliance also comprises a member for collecting pollen from said at least one donor plant, a member for diffusing the pollen over at least one receiver plant, and a channel for conveying the pollen collected from the collecting member to the diffusion member. The flow amplifier 10 is disposed in the conveying channel in order to move the pollen through this conveying channel.

The invention claimed is:

1. A Coanda effect flow amplifier for bringing about an amplified gas flow, comprising:

a main air circulation duct, at least one injection orifice opening into the main duct, a plurality of orifices for feeding compressed driving gas, each being configured to be connected to a source of compressed driving gas in order to feed said at least one injection orifice with compressed driving gas, at least one distribution duct connecting said plurality of feed orifices to said at least one injection orifice, an amplification profile at least partially delimiting said at least one injection orifice and forming a convex surface configured to bring about a Coanda effect in a flow of compressed driving gas injected through said at least one injection orifice.

2. The flow amplifier as claimed in claim 1, wherein the main air circulation duct extends along a circulation axis, said at least one distribution duct forming an annular distribution cavity extending along and around the circulation axis, said at least one injection orifice forming a slot extending at least partially around the circulation axis.

3. The flow amplifier as claimed in claim 2, wherein a radial dimension of the slot is limited by the presence of a connecting radius exhibited by a deflecting wall facing each of the feed orifices, this deflecting wall being adjacent to the slot opening onto the injection orifice.

4. The flow amplifier as claimed in claim 2, wherein said at least one injection orifice is formed by an annular injection cavity extending around the circulation axis and radially with respect to this circulation axis.

5. The flow amplifier as claimed in claim 2, wherein the feed orifices are oriented transversely to the circulation axis, the flow amplifier also comprising at least one deflecting wall facing each of the feed orifices.

6. The flow amplifier as claimed in claim 1, comprising a plurality of mutually independent distribution ducts and a plurality of injection orifices, each distribution duct extending between at least one of the plurality of feed orifices and at least one of the plurality of injection orifices so that it is possible to inject separate flows of compressed driving gas through the plurality of injection orifices.

7. The flow amplifier as claimed in claim 6, wherein said at least one injection orifice is formed by an annular injection cavity extending around the circulation axis and radially with respect to this circulation axis, wherein said plurality of distribution ducts is formed by the annular distribution cavity, the flow amplifier also comprising at least two partition elements for compartmentalizing the distribution cavity so as to form at least two independent distribution ducts.

8. The flow amplifier as claimed in claim 1, further comprising means for adjusting a flow cross section for the driving gas of said at least one injection orifice so as to regulate the flow rate of driving gas passing through said at least one injection orifice.

9. The flow amplifier as claimed in claim 6, further comprising means for adjusting a flow cross section for the driving gas of said at least one injection orifice so as to regulate the flow rate of driving gas passing through said at least one injection orifice, and wherein the adjusting means are configured to separately adjust the flow cross section for driving gas of at least two injection orifices communicating with independent distribution ducts so that it is possible to inject flows of compressed driving gas with different flow rates through said at least two orifices.

10. The flow amplifier as claimed in claim 1, wherein the plurality of injection orifices comprises at least one first and at least one second injection orifice, which are intended to be disposed respectively in the lower part and in the upper part of the main air circulation duct so that it is possible to bring about a different amplified air flow rate in the lower and upper parts.

11. The flow amplifier as claimed in claim 1, wherein the adjusting means are configured to separately adjust the flow cross section for driving gas of at least four injection orifices communicating with independent distribution ducts, the plurality of injection orifices also comprising at least one third and at least one fourth injection orifice, which are intended to be disposed respectively at opposite lateral parts of the main air circulation duct.

12. The flow amplifier as claimed in claim 1, comprising:

a body in which said main air circulation duct, the plurality of feed orifices, said at least one distribution duct, the amplification profile and a first portion of said at least one injection orifice are formed, an injection ring forming a second portion of said at least one injection orifice, the injection ring being configured to be disposed facing the body, the first and second portions of said at least one injection orifice facing one another, the distance between the first and second portions of said at least one injection orifice defining a flow cross section for driving gas through said at least one injection orifice.

13. The flow amplifier as claimed in claim 1, further comprising means for adjusting a flow cross section for the driving gas of said at least one injection orifice so as to regulate the flow rate of driving gas passing through said at least one injection orifice, and wherein the adjusting means are configured to adjust the distance between the injection ring and the body so as to vary the flow cross section for driving gas of said at least one injection orifice.

14. The flow amplifier as claimed in claim 1, wherein the ring is movable with respect to the body about at least one axis transverse to a circulation axis of the main circulation duct, the adjusting means being configured to adjust the inclination angle of the ring with respect to said at least one transverse axis so as to vary the flow cross section for driving gas of said at least one injection orifice asymmetrically.

15. The flow amplifier as claimed in claim 1, wherein said flow amplifier is configured to be incorporated into an aeraulic apparatus for pollinating at least one receiver plant with pollen collected from at least one donor plant that includes a member for collecting the pollen from said at least one donor plant, a member for diffusing the pollen over at least one receiver plant, and a channel for conveying the pollen collected from the collecting member to the diffusing member or members.

16. The flow amplifier as claimed in claim 1, wherein said flow amplifier is configured to amplify an air flow comprising particles exhibiting a predetermined sedimentation rate, wherein the Coanda effect flow amplifier brings about an air flow inside the main circulation duct, the speed of which is higher than the predetermined sedimentation rate.

17. The flow amplifier as claimed in claim 16, wherein the speed of the air flow brought about inside the main circulation duct is less than or equal to 10 $m \cdot s^{-1}$.

18. The flow amplifier as claimed in claim 17, wherein the speed of the air flow brought about inside the main circulation duct is less than or equal to 5 $m \cdot s^{-1}$.

* * * * *